United States Patent [19]

Morse

[11] 4,438,263

[45] Mar. 20, 1984

[54] CELLULOSE GRANULES AND PROCESS FOR PRODUCING THE SAME

[75] Inventor: Erwin E. Morse, Berlin, N.H.

[73] Assignee: James River Corporation of Virginia, Richmond, Va.

[21] Appl. No.: 405,992

[22] Filed: Aug. 6, 1982

[51] Int. Cl.$^3$ .......................... C08B 1/00; D21C 9/00; D21C 9/18
[52] U.S. Cl. ..................................... 536/56; 264/117; 424/362
[58] Field of Search .......................... 536/56; 424/362; 264/117; 162/157C

[56] References Cited

U.S. PATENT DOCUMENTS

| | | | |
|---|---|---|---|
| 2,580,491 | 1/1952 | Ward et al. | 536/56 |
| 2,743,220 | 4/1956 | Estes | 536/56 |
| 3,146,168 | 8/1964 | Battista | 536/56 |
| 3,345,357 | 10/1967 | Cruz | 536/56 |
| 3,826,711 | 7/1974 | Schoggen et al. | 162/157 C |
| 4,040,856 | 8/1977 | Litzinger | 162/157 C |
| 4,269,859 | 5/1981 | Morse | 536/56 |

FOREIGN PATENT DOCUMENTS 2518270 3/1976 Fed. Rep. of Germany ...... 424/362

Primary Examiner—Ronald W. Griffin
Attorney, Agent, or Firm—Gordon W. Hueschen

[57] ABSTRACT

The invention relates to a process for producing essentially pure cellulose granules which comprises treating finely-divided particles of essentially pure cellulose in aqueous suspension with an agglutinating reagent which promotes agglutination of said particles, causing said particles to agglutinate, and mechanically separating the agglutinated cellulose particles from the suspension medium leaving a wet mass of agglutinates, washing said wet mass with water until said agglutinating reagent has been removed therefrom, leaving a second wet mass consisting essentially of agglutinated cellulose particles and water, and displacing the water with a solvent which is solvent for water but non-solvent for cellulose, and removing the water from said second wet mass by a non-evaporative procedure wherein coalescence of said agglutinated particles is prevented and said agglutinated particles dry into discrete granules of essentially pure cellulose.

20 Claims, No Drawings

CELLULOSE GRANULES AND PROCESS FOR PRODUCING THE SAME

BACKGROUND OF THE INVENTION

1. Field of Invention

The invention relates to cellulose granules and to a process for producing the same and is particularly directed to cellulose granules which are suitable for use as an excipient in tableting, especially by the direct compression method, and to a process for producing the same.

2. Prior Art

Flocked cellulose materials, in the form of subdivided fibers or fiber fragments having varying degrees of fiber characteristics, have found use in the pharmaceutical industry as binders and disintegrants in the making of pharmaceutical tablets. Such materials have found use in the two-stage process known as wet granulation, in which the various ingredients are first blended with a moistening liquid to form a pasty mass which is then sized through a coarse sieve. The wet granules are then dried and, if necessary, broken up again in a hammermill and resized to the desired mesh size of, for example, twenty-five to one hundred (25–100) mesh. The finished granules are then in a condition which permits adequate flow rates in a formulated pharmaceutical preparation from the feed hopper to the tablet dies of a compressing machine.

Another approach to the manufacture of tablets is by the direct compression method, in which the ingredients are merely dry blended by simple admixture and then fed directly to tableting dies. This method offers substantial savings in time and equipment, but an absolute requisite for employment of this process is that all ingredients have a high order of fluidity. It is in this area of direct compression tablet production that previously-available flocked cellulose materials fall down. The previously-available materials fail to fulfill the requisites for compression tablet making to an adequate extent. These requisites are as follows: The material must be free-flowing, it must have binding properties, and it must not stick to punches or dies. These requirements are taken from page fifteen of the text entitled "Tablet Making" by Arthur Little and K. A. Mitchell, Second Edition, The Northern Publishing Co., Ltd., Liverpool, England, 1968. In addition, the tablets produced must disintegrate readily in aqueous or gastric solution.

Microcrystalline cellulose has been the most commercially acceptable such excipient, but there is considerable room for improvement in respect to its cost and its flow and disintegration characteristics. Also, dry-granulated flocked cellulose according to U.S. Pat. No. 4,269,859 has found use as such an excipient but its color, compressibility, and uniformity of performance from batch to batch has left room for considerable improvement.

Thus, since the previously-available cellulose materials do not fill these requisites, it has become desirable to find another form of cellulose which may be employed in the direct compression manufacture of tablets, which is free-flowing and particulate and still able to impart the necessary degree of binding to the tablet ingredients and which, although imparting a certain requisite degree of hardness to the tablet, also permits the formed tablet to disintegrate at an adequate rate in aqueous or gastric solution. The problem is thus to provide a cellulose material of adequate fluidity and a method of transforming existing materials of an intransigent, non-flowing particulate nature into a form which flows readily but without compromising its chemical nature by the addition of foreign matter such as gum or other binding agent.

Such novel form of cellulose and method of producing the same are provided according to the present invention.

Of course, any cellulose material must meet additional requirements if it is to be used in pharmaceutical tableting, for example, all of the usual tests listed for Powdered Cellulose in the National Formulary, Volume XV, page 1219 and, if the end product is to be ingested by a human, then cellulose material must meet additional requirements as set forth in the Food Chemical Codex, Third Edition, pages 80–81. Such additional requirements are of course well known to one skilled in the art and, it goes without saying, form no part of the present invention, but will of course be included among the characteristics of the cellulose product of the invention if to be employed according to such high-requirement standards.

OBJECTS OF THE INVENTION

It is an object of the present invention to provide a novel cellulose material which is useful in tableting, which has uniformly good flow and binding characteristics, and which is accordingly useful in direct compression tableting. It is a further object of the invention to provide a method for obtaining such highly desirable form of cellulose. It is another object of the invention to provide such cellulose materials having the aforesaid desirable characteristics, in the form of granules having a specified particle size by the agglutination of cellulose fibers having an average length on their largest dimension between about twenty (20) and about sixty (60) microns, and preferably between about thirty (30) and about forty (40) microns. Other objects of the invention are to avoid the disadvantages of the prior art and to obtain such advantages as will become apparent hereinafter. Still others will be apparent to those skilled in the art.

SUMMARY OF THE INVENTION

The invention relates to a process for producing essentially pure celluose granules which comprises treating finely-divided particles of essentially pure cellulose in aqueous suspension with an agglutinating reagent which promotes agglutination of said particles, causing said particles to agglutinate, and mechanically separating the agglutinated cellulose particles from the suspension medium leaving a wet mass of agglutinates, washing said wet mass with water until said agglutinating reagent has been removed therefrom, leaving a second wet mass consisting essentially of agglutinated cellulose particles and water, and removing the water from said second wet mass by a non-evaporative procedure wherein coalescence of said agglutinated particles is prevented and said agglutinated particles dry into discrete granules of essentially pure cellulose.

In a preferred form of the invention, the particles are caused to agglutinate by drowning the suspension in water and in which the thus-agglutinated particles are separated from the suspension by filtration to form said second wet mass.

In one form of the invention the water is removed from the second wet mass by sublimation, that is to say, the second wet mass is subjected to lyophilization or freeze-drying. By this procedure, the cellulose agglutinates are dried into discrete granules and coalescence, such as occurs when the water is evaporated, is avoided.

In a preferred form of the invention, however, the water is removed from said second wet mass as a solution thereof in an inert, low-boiling, organic solvent which is solvent for water and is non-solvent for cellulose. This aspect of the invention comprises one or more further features in which said solvent is water-miscible, in which said water-miscible solvent is an alcohol or ketone, in which said solvent is acetone, or in which said solvent is methanol or isopropanol.

The agglutinating reagent can be any substance which has a solubilizing or parchmentizing effect on cellulose. Those skilled in the art, having in mind that the purpose of the agglutinating reagent is to cause the surface of the cellulose particles to become sticky or tacky so that the particles will agglutinate into clumps or agglutinates, are cognizant of a wide variety of solubilizing and parchmentizing substances which can be used for this purpose. In general, however, it may be said that such materials are preferably selected from the class consisting of alkali metal hydroxide, zinc chloride, cupriethylene diamine, sodium zincate, iron-sodium tartrate complex, lithium chloride, stannous chloride, sulfuric acid, and phosphoric acid.

In a preferred form of the invention, the agglutinating reagent is an alkali metal hydroxide such as potassium or lithium hydroxide preferably sodium hydroxide.

Advantageously, the concentration of sodium hydroxide is between about 7 and about 11 percent. It will be understood, however, that even with closely related materials such as potassium and lithium hydroxide, a different amount may be required. Thus, with lithium hydroxide, superior results are obtained within the range of about 4 to about 8 percent (limit of solubility) whereas, with potassium hydroxide, best results are obtained within the range of about 30 to about 35 percent potassium hydroxide.

Similarly, with the various other materials mentioned above, the amount required to obtain the desired degree of tackiness on the surface of the particles will vary widely. It will also be understood, however, that those skilled in the art can determine suitable concentrations either by observing which concentrations give granules and which do not, or by exposing the cellulose to different concentrations and observing the effect of the different concentrations in producing a tacky surface on the cellulose particles.

In accordance with the practical aspects of the invention, the concentration of the suspension with regard to cellulose particles can also have an effect on the agglutinating process. Thus, it is possible to produce such a dilute dispersion of cellulose particles that agglutination is precluded or largely prevented. In a preferred aspect of the invention it is accordingly desirable to keep the concentration of the cellulose in the solution of agglutinating reagent realatively high, such that, for example, in the case of sodium hydroxide solution, the ratio of sodium hydroxide solution to cellulose particles is between about 0.5 and 2.5. This concentration or ratio will vary according to the particular agglutinating reagent and will have to be determined in each case by suitable tests, but in any event the concentration must be such that effective agglutination is obtained.

While the invention is applicable to any kind of particulate cellulose, it is preferred to start with fibrous cellulose having a particle size between about 20 and about 60 microns, preferably between about 30 and about 40 microns.

The invention also is directed to essentially pure cellulose granules suitable for use as an excipient in tableting, characterized as a mass of discrete granules of essentially uniform size and character and by the following properties: a flow rate of at least about 5 grams per second, preferably between about 20 and about 40 grams per second, as measured in a Flo-Graph TM through the ⅝ inch orifice; a size such that between about 15 to about 80 percent is retained on a 100 mesh screen when 25 grams is sieved in a Ro-Tap TM apparatus for 25 minutes; a compressibility measured as hardness in Strong-Cobb units of at least about 20, preferably about 28, to No-Break when 0.4 gram of material predried at 105 degrees Centigrade is compressed into 7/16 inch diameter tablets under 1000 pounds load and the tablets tested in Model 2E Schleuniger Hardness Tester; a disintegration time in water without agitation of between about 2 and about 20 seconds for tablets prepared as above; and a bulk density of less than about 4 ml./gm; and especially to such a product in which the granules are composed of cellulose fibers having a particle size of between about 20 to about 60 microns, preferably about 30 to about 40 microns; the flow rate is between about 20 and about 40 grams per second; the size is such that about 40 to about 60 percent is retained on a 100 mesh screen; the compressibility measured as hardness in Strong-Cobb units is about 28 to No-Break; and the disintegration in water is about 5 to about 10 seconds.

The range of 15 to 80 percent on a 100 mesh screen includes materials having a high degree of granularity as well as those having a low degree. Usually best results are obtained in the range of about 40 to 60 percent of the product on 100 mesh. The granularity contributes to good flow properties, but no exact distribution of particle sizes is required in order for the product to be useful and effective. A large proportion of particles that are finer than 200 mesh, preferably not more than about 25 percent, is undesirable, however, because then the flow rate suffers. If a multiple screen is used, the total retained on the 100 mesh screen is the sum of the amount on that screen plus the amounts retained on all coarser screens.

Suitable starting materials for carrying out the process of the present invention and for production of the cellulose granules of the present invention are members of a family of fibrous and powdered cellulose materials produced by the James River Corporation of Berlin, N.H., and sold under their trademark Solka-Floc TM. Both food and pharmaceutical grades of this Solka-Floc TM product are available. Other cellulosic raw materials of similar nature and grade can of course also be employed. According to the invention the cellulose fibers of the starting cellulose material have an average length on their largest dimension of between about twenty (20) and about sixty (60) microns, advantageously between about thirty (30) and about forty (40) microns. Due to their toughness and resiliency, the fibers of this starting floc material do not undergo any essential change in these dimensions during processing according to the process of the present invention into the granular compositions of the invention.

Suitable cellulose floc and powder materials which can be employed as starting materials in the process of the invention and to make cellulose granules of the present invention, and some of their characteristics, are set forth in Table I. As already stated, similar cellulose products having essentially the same properties and consisting essentially of cellulose fibers having an average length on their largest dimension of between about twenty (20) and about sixty (60) microns, preferably between about thirty (30) and about forty (40) microns, can be used equally as well as the Solka-Floc ™ James River Corporation products as set forth in Table I.

TABLE I

Characteristics of Some Representative Starting Cellulose Powders

The Solka-Floc ™ (Alpha-Floc ™ in Canada) products are pure, white, finely-divided cellulose fragments of natural cellulose fibers, made from highly purified wood pulp. Fiber length is essentially unchanged in granules made therefrom. The dry products are at least 99.5% cellulose, virtually lignin free, and have no relation to wood flour. Their pH value falls within a neutral range, and their brightness and color remain stable over extended periods. The subdivided fibers or fiber fragments contain no obvious foreign material and have a slight, characteristic odor similar to standard. Grades BW-40 and BW-60 are slightly fibrous, and the remaining grades are relatively "free-flowing" powders.

The specified values of a number of properties listed below do not differ from one grade to another. The principal differences between grades are in bulk and in screen analysis.

| | |
|---|---|
| pH (10% suspension) | 5.0–7.5 |
| Loss on Drying, % | NMT 7 |
| Residue on Ignition, % | NMT <0.3 |
| Water Soluble Substances, % | NMT 1.5 |
| Heavy Metals, % | NMT 0.001 |
| Starch | Absent |

| | | Screen Analysis (Ro-Tap ™, Tyler) | | Average Particle |
|---|---|---|---|---|
| Grade | Bulk (ml/gm) | on 35 mesh | Thru 100 mesh | Thru 200 mesh | Size (microns) |
| BW-40NF | 3.0 ± 0.5 | LT 5 | NLT 70 | NLT 40 | 55–65 |
| BW-60NF | 2.5 ± 0.3 | LT 1 | NLT 80 | NLT 45 | 45–55 |
| BW-100NF | 2.0 ± 0.3 | LT 1 | NLT 85 | NLT 70 | 35–45 |
| BW-200NF | 2.1 ± 0.1 | LT 0.5 | NLT 90 | NLT 75 | 30–40 |
| BW-2030NF | 2.1 ± 0.1 | LT 0.5 | NLT 90 | NLT 75 | 30–40* |

| | Screen Analysis (Alpine Air-Jet ™ Sieve) | |
|---|---|---|
| | Thru 200 mesh | Thru 400 mesh |
| BW-300FCC | 2.2 ± 0.3 | NLT 99 | NLT 95 | 15–25 |

*Residue on ignition = <0.2%

DESCRIPTION OF THE PREFERRED EMBODIMENTS

The following examples are given by way of illustration only, and are not to be construed as limiting. The parts and percentages are by weight unless otherwise specified.

EXAMPLES 1–4

Cellulose Granules, Including Comparative Examples or Controls

Various grades of starting cellulose floc were dispersed in 8% aqueous sodium hydroxide solution and mixed thoroughly by stirring over a period of about five (5) minutes and then drowned in three or four volumes of water while continuing the stirring. The floc was then immediately separated on a coarse, sintered glass filter (a centrifuge can be used if desired), followed by washing with water until the rinsings were found to be free of sodium hydroxide and then with successive portions of isopropanol until the bulk of the water was removed, after which suction was applied to the filter to remove as much of the isopropanol and what water it contained, and the product removed and dried in an oven at 105° Centigrade. After drying, the product was sieved through a U.S. standard No. 40 screen.

The results of the testing showed that compaction (Chilsonated) granulated Solka-Floc ™ and microcrystalline cellulose (Avicel ™ PH 101 and 102, FMC Corporation) were unsatisfactory in one or more of the several categories tested and that granulated cellulose produced according to the invention (Examples 1, 2, 3, and 4) had good color, good flow, high compressibility, rapid disintegration, and high compaction strength.

The results obtained are summarized in Tables II and IIA. Table II gives data of different products of the invention in comparison with prior art products and Table IIA roughly equates qualitative observations of flow rates with quantitative measurements.

TABLE IIA

| Flow Rate | | |
|---|---|---|
| Qualitative | Quantitative Gms./Sec. | Tapping Required to Aid Flow |
| Very Good | 30–40 | No |
| Good | 20–30 | No |
| Fair | 10–20 | Yes |
| Poor | <10 | Yes |

TABLE II

| Example | Starting Material Solka-Folc- ™ | Color | Flow Rate (gms./sec) (a) | Size % on 100 mesh screen (b) | Bulk Density ml/gm. | 8% NaOH/ Cellulose | Compressibility 1000 pounds (c) | Disintegration seconds (d) | Compressibility at 5000 pounds 15% Emcopress ™ 13.5 | 50% Acetaminophen (e) |
|---|---|---|---|---|---|---|---|---|---|---|
| 1 Lot 55 | BW-2030 35u | white | very good (30–40) | 41 | 2.5 | 2:1 | 21.5 | 4–6 | 18 | 7.2–7.5 |
| 2 Lot 73 | BW-100 40u | white | good (20–30) | 46 | 2.6 | 2.5:1 | 28 | 10–12 | 28 | 9.5–11.5 |
| 3 Lot 52 | BW-2030 35u + BW-300 22u-1:1 | white | good (20–30) | 51 | 3.2 | 2:1 | >28 | 15–17 | 28 | — |

TABLE II-continued

| Example | Starting Material Solka-Folc- TM | Color | Flow Rate (gms./sec) (a) | Size % on 100 mesh screen (b) | Bulk Density ml/gm. | 8% NaOH/ Cellulose | Compressibility 1000 pounds (c) | Disintegration seconds (d) | Compressibility at 5000 pounds 15% Emcopress TM 13.5 | 50% Acetaminophen (c) |
|---|---|---|---|---|---|---|---|---|---|---|
| 4 Lot 68 | BW-60 50u | white | fair (15–20) | 56 | 3.7 | 1.75:1 | >28 | 10–12 | 22 | 11.0–13.75 |
| Contols Avicel TM PH101 | | off white | poor (<10) | 7 | 2.6 | — | >28 | 50–60 | 22 | 11.0–11.75 |
| Avicel TM PH102 (granular) | | off white | good (20–30) | 24 | 2.7 | — | >28 | 50–60 | 26 | 9.25–11.0 |
| Fine granular Solka-Floc TM (Chilsonated) Lot 1-1-20 | | off white cream | good (20–30) | 81 | 1.6 | — | 5.5 | 18–23 | 13.5 | — | a: Tested in Flo-Graph TM; flow through ⅜" orifice. The fair and poor materials required tapping to aid flow.
b: Tested in Ro-Tap TM apparatus, 25 gms. sieved for 25 minutes.
c: The characteristic of compressibility is measured by the hardness in Strong-Cobb Units of 0.4 gm. tablets, 7/16" in diameter, compressed under stated lbs. load. Hardness measured with Model 2E Schleuniger Tester. Flock pre-dried at 105° C.
d: Time to disintegrate in water without agitation. (0.4 gm., 1000 lbs load).

EXAMPLES 5–13

Following the procedure of Examples 1–4 but varying the concentration of sodium hydroxide, results were obtained as shown in Table III. In all these examples, the starting cellulose material was Solka-Floc TM BW-2030NF and the sodium hydroxide to cellulose ratio was 2:1.

TABLE III
EFFECT OF CONCENTRATION OF NaOH ON GRANULE FORMATION

| Example No. | Concentration NaOH (%) | Granule Formation | Washing rate | Extent of Granule Formation | Compressibility of Product |
|---|---|---|---|---|---|
| 5 | 6% | Yes | Good | Intermediate | Poor-Fair |
| 6 | 7% | Yes | Good | Good | Good |
| 7 | 8% | Yes | Excellent | Good | Good |
| 8 | 9% | Yes | Excellent | Good | Good |
| 9 | 10% | Yes | Excellent | Good | Good |
| 10 | 11% | Yes | Excellent | Good | Good |
| 11 | 13% | Yes | Good | Intermediate | Fair |
| 12 | 15% | Yes | Good | Fair | Fair-Poor |
| 13 | 20% | Yes | Fair | Fair | Fair-Poor |

At lower concentrations of sodium hydroxide, granules were not formed and, at a concentration of 25 percent sodium hydroxide, the extent of granule formation is quite low.

EXAMPLES 14 AND 15

Following the procedure of Table III but substituting the sodium hydroxide by potassium hydroxide, results were obtained as shown in the following table.

TABLE IV
EFFECT OF CONCENTRATION OF KOH ON GRANULE FORMATION

| Example | Concentration KOH (%) | Granule Formation | Washing rate | Extent of Granule Formation | Compressibility of Product |
|---|---|---|---|---|---|
| 14 | 30% | Yes | Fair | Intermediate | Excellent |
| 15 | 35% | Yes | Fair | Intermediate | not tested |

At concentrations of 40 percent and 25 percent and below, granules were not obtained.

EXAMPLES 16, 17, AND 18

Following the procedure of Table III but substituting the sodium hydroxide by lithium hydroxide, results were obtained as shown in the following table.

TABLE V
EFFECT OF CONCENTRATION OF LiOH ON GRANULE FORMATION

| Example | Concentration LiOH (%) | Granule Formation | Washing rate | Extent of Granule Formation | Compressibility of Product |
|---|---|---|---|---|---|
| 16 | 4% | Yes | Excellent | Good | Excellent |
| 17 | 6% | Yes | Excellent | Good | Good to Excellent |
| 18 | 8%* | Yes | Excellent | Good | Good to Excellent |

*limit of solubility of LiOH

At lower concentrations, granules were not obtained.

EXAMPLE 19

Following the procedure of Example 13 but substituting the isopropanol by acetone, results were obtained as shown in the following table:

TABLE VI
SOLVENT DISPLACEMENT WITH SOLKA-FLOC TM BW-200 NF
Comparisons were made with the starting material (Control 1) and with the omission of the acetone washing step (Control 2).

| | Compressibility Tablet* Hardness (Strong-Cobb units) at stated load (lbs) | | | | |
|---|---|---|---|---|---|
| | 500 | 1000 | 2000 | 3000 | 5000 |
| Control 1 | 1 | 5 | 9 | 19 | |
| Control 2 | | 1 | 1 | 2 | 6 |
| Example 19 | 13 | 28+ | NB | NB | |

*0.3 gm. tablets
NB = No Break

These data show that the process of the invention, even when the sodium hydroxide concentration is higher than optimum, gives markedly improved hardness as compared with the starting material and that treatment of the starting material with sodium hydroxide without solvent displacement of the water before drying impaired the compressibility of the material.

EXAMPLES 20, 21, AND 22

Following the procedure of Examples 1-4, with stated variations, results were obtained as shown in the following table:

TABLE VII
SOLVENT DISPLACEMENT WITH STATED GRADES OF SOLKA-FLOC TM

These data show that, without the solvent washing or displacement step, markedly inferior results are obtained.

| Grade of Solka-Floc TM | Treatment | Compressibility Tablet* Hardness (Strong-Cobb units) at stated load (lbs) | | | |
|---|---|---|---|---|---|
| | | 500 | 1000 | 2000 | 3000 |
| Control 3 BW-300 FCC | washed with water. dried at 105° C. | 4 | 7 | 12 | 18 |
| Example 20 | as above, displacing water with isopropanol | 17 | 28+ | NB | NB |
| Control 4 BW-2030 NF | washed with water, dried at 105° C. | 1 | 5 | 11 | 18 |
| Example 21 | as above, displacing water with acetone | 7 | 18 | 27 | NB |
| Control 5 BW-60 NF | washed with water, dried at 105° C. | 1 | 6 | 10 | 18 |
| Example 22 | as above displacing water with acetone | 11 | 24 | 28+ | NB |

*0.4 gm. tablets
NB = No Break

EXAMPLES 23 AND 24

Eleven (11) parts of Solka-Floc TM BW-200 NF was mixed with twenty-one (21) parts of a sixty percent (60%) aqueous solution of zinc chloride (Example 23), and ten (10) parts of Solka-Floc TM BW-200 NF was mixed with twenty (20) parts by volume of a 0.5 molar aqueous solution of cupriethylene diamine (CED) (Example 24) and the resulting mixtures were processed as in Examples 1-4. Zinc chloride is a well-known swelling and tackifying agent for cellulose and is used for making vulcanized (parchment) fiber. CED in high enough concentration, e.g., 0.5 molar, may be used to dissolve cellulose and is used in cellulose concentrations of one-half to one percent in order to measure the solution viscosity of cellulose.

Granule formation was excellent in both cases and the granules formed had good flow characteristics and good compressibility, and the tablets formed therefrom readily disintegrated when dropped into water.

The sixty (60) percent zinc chloride solution was chosen because that is the concentration normally used in making vulcanized fibers and the 0.5 molar CED concentration was chosen because of its known solubilizing action on cellulose. In Example 24, though, the CED was washed out before solubilization of cellulose could take place. A 0.4 molar concentration gave similarly good results but finer granules. When the concentration was too low, e.g., 0.1 to 0.2 molar, no granules were obtained.

These last two Examples show how known properties of materials, known to have a solubilizing or parchmentizing effect on cellulose, can be utilized in selecting suitable concentrations of the agglutinating reagents for use in the process of the invention.

It is to be understood that the invention is not to be limited to the exact details of operation or exact compounds, compositions, methods, or procedures shown and described, as obvious modifications and equivalents will be apparent to one skilled in the art.

I claim:

1. A process for producing essentially pure cellulose granules which comprises:
   treating finely-divided particles of essentially pure cellulose with an agglutinating reagent in aqueous solution which promotes agglutination of said particles;
   causing said particles to agglutinate and mechanically separating the agglutinated cellulose particles from the suspension medium leaving a wet mass of agglutinates;
   washing said wet mass with water until said agglutinating reagent has been removed therefrom, leaving a second wet mass consisting essentially of agglutinated cellulose particles and water; and
   removing the water from said second wet mass by a non-evaporative procedure wherein coalescence of said agglutinated particles is prevented and said agglutinated particles dry into discrete granules of essentially pure cellulose.

2. A process of claim 1, in which said particles are caused to agglutinate by drowning the suspension in water and in which the thus-agglutinated particles are separated from the suspension by filtration to form said second wet mass.

3. A process of claims 1 or 2, in which the water is removed from said second wet mass as a solution thereof in an inert, low-boiling, organic solvent which is solvent for water and is non-solvent for cellulose.

4. A process of claim 3, in which said solvent is water-miscible.

5. A process of claim 1, in which the water is removed from said second wet mass by sublimation.

6. A process of claim 4, in which said water-miscible solvent is an alcohol or ketone.

7. A process of claim 6, in which said solvent is acetone.

8. A process of claim 6, in which said solvent is methanol or isopropanol.

9. A process of claim 1, in which said agglutinating reagent is a substance having a solubilizing or parchmentizing effect on cellulose selected from the class consisting of alkali metal hydroxide, zinc chloride, cupriethylene diamine, sodium zincate, iron-sodium tartrate complex, lithium chloride, stannous chloride, sulfuric acid, and phosphoric acid.

10. A process of claim 1, in which said agglutinating reagent is an alkali metal hydroxide.

11. A process of claim 10, in which said alkali metal hydroxide is sodium hydroxide.

12. A process of claim 11, in which the concentration of sodium hydroxide is between about 7 and about 11 percent.

13. A process of claim 4, in which said water-miscible solvent is an alcohol or ketone and in which said agglutinating reagent is an alkali metal hydroxide.

14. A process of claim 13, in which the concentration of sodium hydroxide is between about 7 and about 11 percent.

15. A process of claim 13, in which the ratio of sodium hydroxide solution to cellulose particles in said suspension is between about 0.5 and about 2.5 to 1.

16. A process of claim 1, in which the starting cellulose is fibrous and has a particle size between about 20 and about 60 microns.

17. A process of claim 15, in which the starting cellulose is fibrous and has a particle size between about 30 and about 40 microns.

18. Essentially pure cellulose granules suitable for use as an excipient in tableting, characterized as a mass of discrete granules of essentially uniform size and character and by the following properties:

a flow rate greater than about 5 grams per second, as measured in a Flo-Graph TM through a $\frac{5}{8}$ inch orifice;

a size such that between about 15 to about 80 percent is retained on a 100 mesh screen when 25 grams is sieved in a Ro-Tap TM apparatus for 25 minutes;

a compressibility measured as hardness in Strong-Cobb units of at least 20 to No-Break when 0.4 gram of material predried at 105 degrees Centigrade is compressed into 7/16 inch diameter tablets under 1000 pounds load and the tablets tested in Model 2E Schleuniger hardness tester;

a disintegration time in water without agitation of between about 2 and about 20 seconds for tablets prepared as above; and a bulk density of less than about 4 ml./gm.

19. The product of claim 18, in which the cellulose granules are composed of cellulose fibers having a particle size between about 20 and about 60 microns, the flow rate is about 20 to 40 grams per second, the size is such that about 40 to about 60 percent is retained on a 100 mesh screen, the compressibility measured as hardness in Strong-Cobb units is about 28 to No-Break, and the disintegration in water is about 5 to about 10 seconds.

20. The product of claim 19, in which the cellulose granules are composed of celluose fibers having a particle size between about 30 and about 40 microns.

* * * * *

UNITED STATES PATENT AND TRADEMARK OFFICE
CERTIFICATE OF CORRECTION

PATENT NO. : 4,438,263
DATED : March 20, 1984
INVENTOR(S) : Erwin E. Morse

It is certified that error appears in the above—identified patent and that said Letters Patent is hereby corrected as shown below:

Col. 2, line 35; after "size" insert -- , --

Col. 2, line 47; "celluose" should read -- cellulose --

Col. 3, line 31; after "hydroxide" (first occurrence) insert -- , --

Col. 3, line 61; "realatively" should read -- relatively --

Col. 4, line 13; delete "the" and insert -- a --

Cols. 5 & 6 in Table II and 7 & 8 in Table II-continued, the second column heading, line 4; "Folc$^{TM}$" should read -- Floc$^{TM}$ --

Cols. 5 & 6 in Table II and 7 & 8 in Table II-continued, the heading over the last two columns, line 1; "Compresibility" should read -- Compressibility --

Cols. 7 & 8 in Table II-continued, column 1, line 3; "Contols" should read -- Controls --

Col. 12, line 19; "celluose" should read -- cellulose --

Signed and Sealed this

Twenty-fifth Day of September 1984

[SEAL]

Attest:

GERALD J. MOSSINGHOFF

Attesting Officer

Commissioner of Patents and Trademarks